United States Patent
Kopp

(10) Patent No.: US 9,097,641 B2
(45) Date of Patent: Aug. 4, 2015

(54) METHOD TO DETERMINE THE MASS CONCENTRATION OF PARTICLES IN A DISPERSION INCLUDING PARTICLES AND FLUID

(75) Inventor: Christian Kopp, Planegg (DE)

(73) Assignee: Océ Printing Systems GmbH, Poing (DE)

( * ) Notice: Subject to any disclaimer, the term of this patent is extended or adjusted under 35 U.S.C. 154(b) by 493 days.

(21) Appl. No.: 13/484,773

(22) Filed: May 31, 2012

(65) Prior Publication Data
US 2013/0322903 A1    Dec. 5, 2013

(51) Int. Cl.
*G01N 29/036* (2006.01)
*G01N 29/032* (2006.01)
*G03G 15/10* (2006.01)

(52) U.S. Cl.
CPC ............ *G01N 29/032* (2013.01); *G01N 29/036* (2013.01); *G01N 2291/02416* (2013.01); *G01N 2291/02809* (2013.01); *G03G 15/105* (2013.01)

(58) Field of Classification Search
CPC ................. G01N 2291/02416; G01N 29/036
USPC .............................................. 73/24.01–24.04
See application file for complete search history.

(56) References Cited

U.S. PATENT DOCUMENTS

| | | | | |
|---|---|---|---|---|
| 2,926,522 A * | 3/1960 | Kritz | | 73/32 R |
| 3,844,174 A * | 10/1974 | Chabre | | 73/865.5 |
| 4,497,208 A * | 2/1985 | Oja et al. | | 73/584 |
| 5,121,629 A | 6/1992 | Alba | | |
| 5,129,255 A * | 7/1992 | Corbin | | 73/24.02 |
| 5,245,290 A | 9/1993 | Cannon et al. | | |
| 5,616,872 A * | 4/1997 | O'Brien | | 73/865.5 |
| 6,109,098 A * | 8/2000 | Dukhin et al. | | 73/64.42 |
| 6,449,563 B1 * | 9/2002 | Dukhin et al. | | 702/22 |
| 6,617,070 B1 * | 9/2003 | Morrissey et al. | | 429/105 |
| 6,817,229 B2 | 11/2004 | Han et al. | | |
| 6,898,978 B2 * | 5/2005 | O'Brien et al. | | 73/613 |
| 7,764,891 B2 | 7/2010 | Du et al. | | |
| 2006/0093404 A1 * | 5/2006 | Chou et al. | | 399/237 |
| 2006/0150836 A1 | 7/2006 | Berg et al. | | |
| 2008/0279597 A1 | 11/2008 | Berg et al. | | |
| 2009/0078050 A1 * | 3/2009 | Sinha | | 73/632 |
| 2011/0058838 A1 | 3/2011 | Ritzer et al. | | |

OTHER PUBLICATIONS

Babchin et al., "Electrokinetci Measurements by Electroacoustical Methods," 1989, Advance in Colloid and Interface Science, 30 pp. 111-151.*

(Continued)

*Primary Examiner* — John Fitzgerald
(74) *Attorney, Agent, or Firm* — Schiff Hardin LLP

(57) ABSTRACT

In a method to determine particle mass concentration in a dispersion having particles and fluid, the dispersion in a measurement cell is exposed to an alternating field of variable frequency to set the particles into oscillation to generate sound pressure waves. Amplitudes of the sound pressure waves are measured depending on the frequency so that a maximum amplitude of the sound pressure waves is established and a frequency associated with the amplitude is determined as a resonance frequency of the sound pressure wave. The mass concentration of the particles in the dispersion is established from the resonance frequency.

10 Claims, 3 Drawing Sheets

(56) References Cited

OTHER PUBLICATIONS

"Effect of Particle Size Distribution and Aggregation on Electroacoustic Measurements of ζ Potential," James et al., American Chemical Society, vol. 8 (1992), pp. 420-423.

"A New Formula for the Dynamic Mobility in a Concentrated Colloid," O'Brien et al., Colloids and Surfaces A: Physicochem. Eng. Aspects 218 (2003) pp. 89-101.

* cited by examiner

METHOD TO DETERMINE THE MASS CONCENTRATION OF PARTICLES IN A DISPERSION INCLUDING PARTICLES AND FLUID

BACKGROUND

A liquid developer that is used in electrophoretic printing is used as an example of such a dispersion. This has as particles toner particles that are dispersed in a carrier fluid as a fluid. In the following the preferred embodiment is essentially explained using a liquid developer, without therefore limiting the preferred embodiment to liquid developer.

For single-color or multicolor printing of a printing substrate (for example a single sheet or a belt-shaped recording material), it is known to generate image-dependent charge images on a charge image carrier, which charge images correspond to the images to be printed (comprising regions to be inked and regions that are not to be inked). The regions of the charge images that are to be inked are revealed as toner images on the charge image carrier via toner particles with a developer station. The toner image that is thereby generated is transported via a transfer station to the printing substrate and transfer-printed onto the printing substrate at a transfer printing point. The toner images are fixed on the printing substrate in a fixing station.

A liquid developer having at least charged toner particles and carrier fluid can be used to ink the charge images. A method for such an electrophoretic printing in digital printing systems is known from U.S. 2006/0150836 A1 or U.S. 2008/279597 A1, for example. After the charge images of the images to be printed have been generated on the charge image carrier, these are inked with toner particles into toner images via a developer station. A carrier fluid including a silicone oil as a liquid developer with color particles (toner particles) dispersed therein is thereby used here. The supply of the liquid developer to the charge image carrier can take place via a developer roller that is supplied with liquid developer from a reservoir with liquid developer. The image film generated in the development on the charge image carrier is subsequently accepted by the charge image carrier via a transfer unit and transferred onto the printing substrate in a transfer printing zone.

In this printing method, using the liquid developer the process of electrophoresis is employed to transfer toner particles to the printing substrate in the carrier fluid. The solid, electrically charged toner particles thereby migrate through the carrier fluid as a transport medium, wherein the transport can be controlled via an electrical field between the transfer roller and the printing substrate. In addition to the toner particle charge and the electrical field, the provision of a sufficiently thick carrier fluid layer through which the toner particles can migrate and a sufficient concentration of the toner particles in the carrier fluid are a requirement for this.

The liquid developer used in the printing apparatus can be mixed together in the developer station (in a mixing unit, for example) from a toner concentrate (comprising toner and carrier fluid) carrier fluid. For a trouble-free print image it is necessary that sufficient toner particles are included in the liquid developer, and thus the toner mass concentration in the liquid developer has the provided value. It must thereby be taken into account that, in the printing operation, liquid developer is removed from the mixing unit and is partially applied to the printing substrate.

A defined toner mass concentration and electrophoretic mobility of the toner particles in the carrier fluid is required for a successful and uninterrupted development of the charge images.

The adjustment of the toner mass concentration and mobility of the toner particles in the carrier fluid requires that the toner mass concentration and the mobility of the toner particles can be determined in the developer station. Given a relevant toner mass concentration (for example in the range of 2% to 40% of the liquid developer), electroacoustic methods for the determination of the electrophoretic mobility of toner particles are known that, however, assume a precise knowledge of the toner mass concentration.

From U.S. 2011/058838 A1 a method is known according to which the toner mass concentration in a liquid developer can be determined. For this the liquid developer is charged with at least one ultrasound wave. It is thereby assumed that the sound velocity of the sound propagating in the liquid developer essentially depends on the proportion of the toner particles in the carrier fluid within predetermined temperature limits and constant carrier fluid. The delay of an ultrasound wave in the liquid developer is accordingly measured along a predetermined measurement path, and the sound velocity—which is a measure of the toner mass concentration in the liquid developer—can be determined from this. By measuring the delay of the sound wave in the liquid developer, its toner mass concentration can thus be determined. Given a plurality of liquid developers with known toner mass concentrations, the correlation between the delay of an ultrasound wave and the toner mass concentration can be determined via calibration processes under consideration of the temperature of the liquid developer, and the determined values with regard to delay and toner mass concentration can be stored in a table, for example. By measuring the delay of a sound wave through a liquid developer, this table can be used in order to determine its toner mass concentration. If necessary an interpolation can be made between the values in the table. Comparable methods to determine the mass concentration in dispersions are known from U.S. Pat. Nos. 6,817,229 B2, 5,121,629 A or 7,764,891 B2, for example.

A measurement apparatus to determine the electrophoretic mobility of electrically charged particles in a fluid is known from U.S. Pat. No. 5,245,290 A. A dispersion to be tested that includes electrically charged particles whose mobility should be established is contained in a measurement cell. An alternating electrical field that excites the particles in the fluid to oscillate is applied to the measurement cell. The oscillating particles generate sound waves whose velocity can be assessed. The electrophoretic mobility of the particles can be concluded from the electrical field and the average velocity of the particles in the fluid. A formula to calculate the dynamic mobility of particles in a dispersion can be learned from R. W. O'Brien et al./Colloids and Surfaces A: Physiochem. Eng. Aspects 218 (2003) P. 89-101.

In the known measurement methods, either the mass concentration or the electrophoretic mobility of particles is measured in various measurement cells and with various sample volumes, wherein concentration and temperature differences lead to a reduced measurement precision.

SUMMARY

It is an object to specify a method with which the mass concentration of particles in a dispersion and additionally their electrophoretic mobility in the dispersion as well can be determined in a measurement process. The dispersion has fluid in which particles are dispersed.

In a method to determine particle mass concentration in a dispersion having particles and fluid, the dispersion in a measurement cell is exposed to an alternating field of variable frequency to set the particles into oscillation to generate sound pressure waves. Amplitudes of the sound pressure waves are measured depending on the frequency so that a maximum amplitude of the sound pressure waves is established and a frequency associated with the amplitude is determined as a resonance frequency of the sound pressure wave. The mass concentration of the particles in the dispersion is established from the resonance frequency.

DESCRIPTION OF A PREFERRED EXEMPLARY EMBODIMENT

Figure 1:
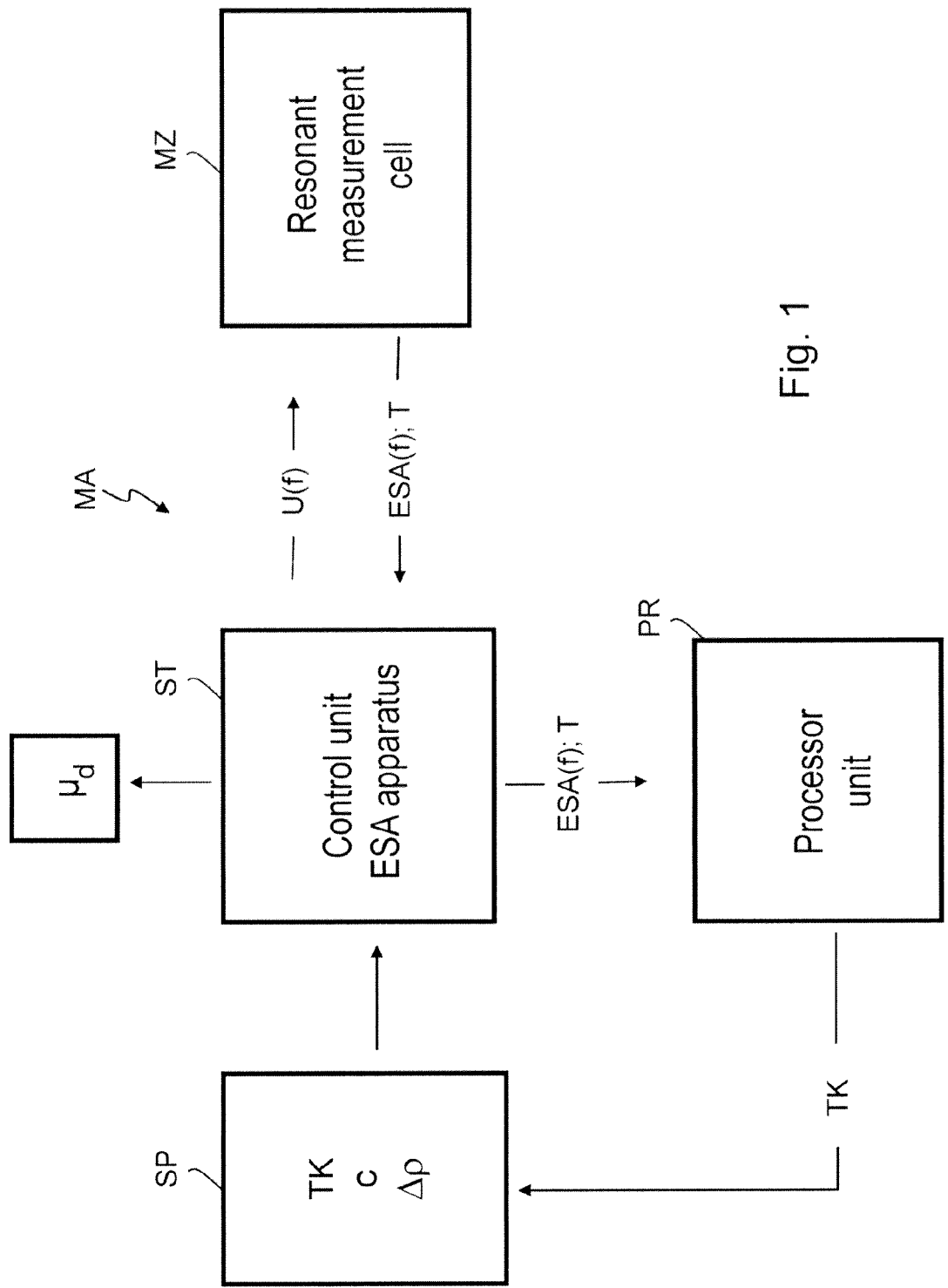
FIG. 1 illustrates a measurement arrangement to determine the mass concentration and the dynamic mobility of particles in a dispersion.

For the purposes of promoting an understanding of the principles of the invention, reference will now be made to the preferred exemplary embodiment/best mode illustrated in the drawings and specific language will be used to describe the same. It will nevertheless be understood that no limitation of the scope of the invention is thereby intended, and such alterations and further modifications in the illustrated embodiment and such further applications of the principles of the invention as illustrated as would normally occur to one skilled in the art to which the invention relates are included.

In a measurement cell the dispersion is exposed to an alternating field of variable frequency, for example an alternating electrical field. The particles in the dispersion are set into oscillation by the alternating field, wherein the particles generate sound pressure waves in the dispersion. The amplitudes (ESA signal) of the sound pressure waves are measured depending on the frequencies, wherein the maximum amplitude of the sound pressure waves is established and the frequency associated with this amplitude is determined as a resonance frequency of the sound pressure wave. The mass concentration of the particles in the dispersion is established from the resonance frequency. The dependency of the resonance frequencies on the mass concentrations of the particles in dispersions was previously determined in a calibration process given known mass concentrations of the particles in the dispersion and was stored in a table, for example.

The simultaneous determination of the electrophoretic mobility of the particles in the dispersion is likewise possible with the measurement arrangement since the electrophoretic mobility can be concluded from the ESA signal and the strength of the electrical field (R. W. O'Brien et al./Colloids and Surfaces A: Physiochem. Eng. Aspects 218 (2003) P. 89-101).

An advantage of the method according to the exemplary embodiment is apparent in that the mass concentrations of particles in a dispersion and their mobility in the dispersion can be determined in one measurement process. The result is an improvement of the measurement accuracy for the measurement variables of mass concentration of the particles and electrophoretic mobility of the particles in the dispersion. Transferred to liquid developer, this means that the toner mass concentration and the mobility of the toner particles can be measured with more precision. However, this is decisive for the regulation of these parameters in fluid management of printing systems that use liquid developer to develop the charge images.

In the exemplary embodiment a known measurement arrangement is assumed with which the electroacoustic pressure amplitude (ESA=electroacoustic sonic amplitude) of a sound pressure wave in a dispersion can be measured (U.S. Pat. No. 5,245,290 A).

In the explanation of the exemplary embodiment in the following, a dispersion is discussed that has particles in a fluid, wherein the mass concentration and mobility of the particles in the dispersion should be determined. A liquid developer in an electrographic printer can be used as an example of a dispersion, which liquid developer has toner particles as particles of mineral oil or silicone oil as a liquid, for example, wherein the liquid is called a carrier fluid or carrier.

The exemplary embodiment is explained in further detail in the drawing figures.

FIG. 1 shows in a block diagram an example of a measurement arrangement MA with which the mass concentration TK and the dynamic mobility $\mu_d$ of electrically charged particles in a dispersion can be determined simultaneously. The dispersion is filled into a measurement cell MZ, a specific design of which can be learned from FIG. 2. The dispersion in the measurement cell MZ is exposed to an alternating electrical field U(f), wherein U indicates the voltage and f indicates the frequency of the alternating field. The alternating electrical field sets the particles into oscillation and thereby generates a sound pressure wave in the dispersion. The amplitude of this sound pressure wave (and in addition to this the temperature T in the measurement cell MZ) is emitted as an output signal ESA(f) at the output of the measurement cell MZ. This workflow is controlled by a control unit ST that supplies the alternating voltage U(f) to the measurement cell MZ and receives the ESA signal ESA(f) from this. The control unit ST transmits the ESA signal to a processor unit PR that determines the mass concentration TK of the particles in the dispersion from the ESA signal. The mass concentration TK can be stored in a memory unit SP; the memory unit SP can include as further variables of the dispersion the sound velocity c of the liquid of the dispersion; the viscosity η of the liquid and the density difference Δρ between the particles and the liquid. These variables are supplied to the control unit ST, which determines the dynamic mobility $\mu_d$ of the particles in the dispersion from the variables ESA, TK, c, η and Δρ according to the formula (2) indicated below. The workflow is implemented at a defined temperature T in the measurement cell MZ that is therefore measured in the measurement cell MZ. A change of the temperature T in the measurement cell MZ would lead to changes in the mobility $\mu_d$ of the particles and the amplitude ESA of the sound pressure wave.

Figure 2:
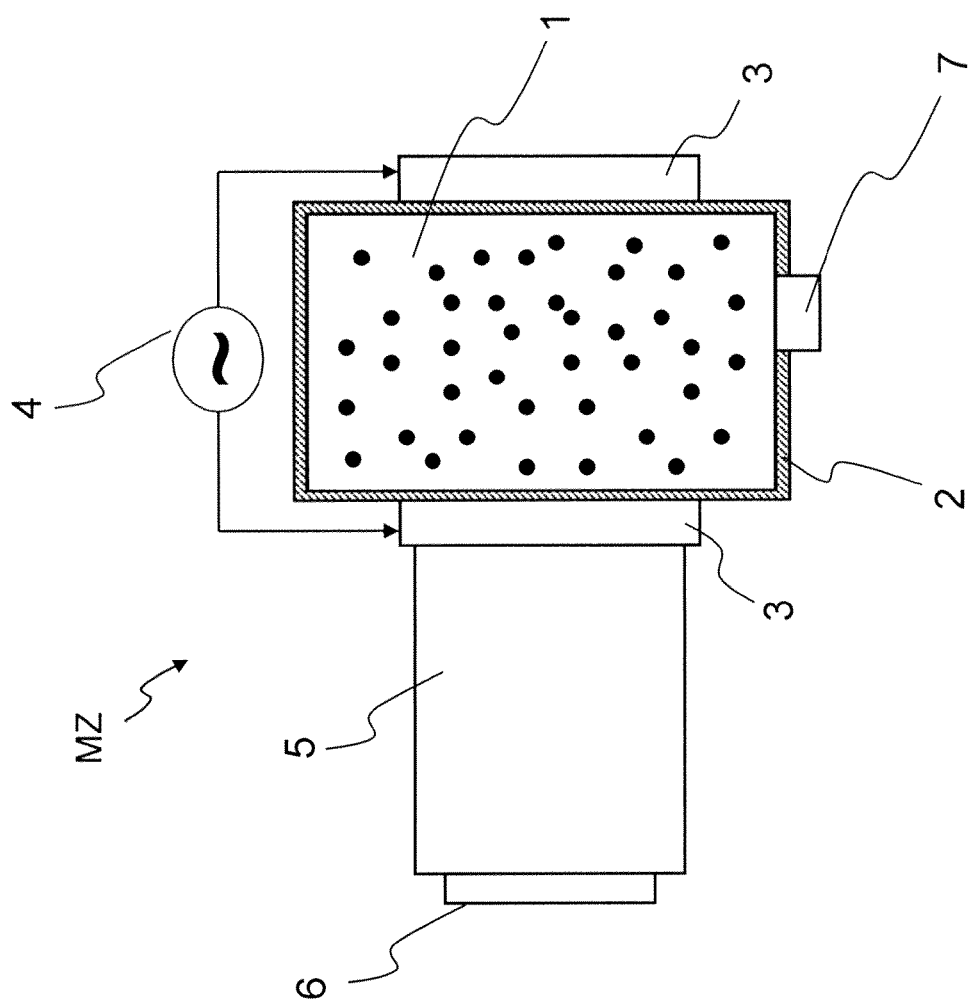
FIG. 2 shows an example of a measurement cell used in the measurement arrangement.

FIG. 2 shows an example of a design of a measurement cell MZ. This has a sample chamber 2 into which a dispersion 1 is filled. The sample chamber 2 comprises a cylindrical acoustic resonator (for example) that is provided with electrodes 3 on parallel surfaces on the sides, between which electrodes 3 an alternating electrical field 4 is applied. Due to the alternating electrical field 4 between the electrodes 3, the electrically charged particles in the dispersion are excited to a periodic movement whose amplitude is maximized by matching or tuning the frequency of the electrical field 4 to the resonance frequency in the sample chamber 2. The oscillating particles thereby generate sound pressure waves in the sample chamber 2, which sound pressure waves can be amplified by an acoustic resonator and have different sound pressure amplitudes depending on the frequency of the alternating field 4. The sound pressure wave that is generated by the alternating field in the dispersion 1 is supplied via a sound conductor rod 5 to a sound pressure transducer 6 that transduces the sound pressure wave into an electrical signal. The amplitude of this signal is determined as an ESA signal depending on the frequencies f of the alternating field 4. In addition to this, the temperature of the sample chamber 2 is also measured by a temperature sensor 7. For example, the sample chamber 2 can have an electrode clearance of ≈3 mm, and an alternating voltage of 80 V with variable frequencies (in the range of ≈1 MHz, for example) can be applied to the electrodes 3.

Figure 3:
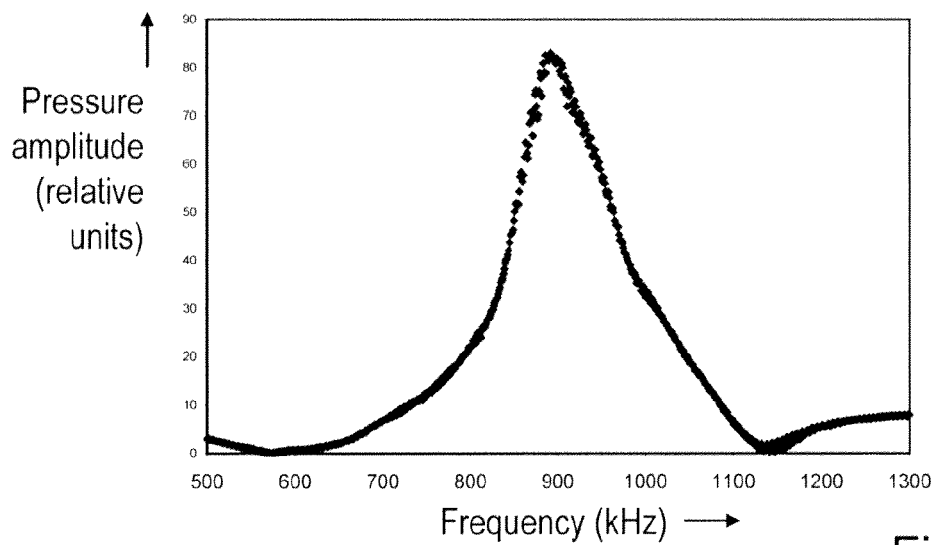
FIG. 3 shows in a diagram, the dependency of the sound pressure amplitude ESA of a sound pressure wave on its frequency in the measurement cell.

The sound pressure amplitude (ESA signal) is thus measured depending on the set frequencies f, wherein the curve progression according to FIG. 3 results as an example (the sound pressure amplitudes are plotted over the frequencies f). The resonance frequency can be determined from this curve progression via a frequency-resolved evaluation. This resonance frequency is established by the geometry of the sample chamber 2 and the acoustic properties of the dispersion. For example, in FIG. 3 the maximum of the sound pressure amplitude ESA lies at a resonance frequency of 891 kHz. In FIG. 3 the sound pressure amplitude is shown depending on the frequency for a liquid developer with toner particles, for example.

Figure 4:
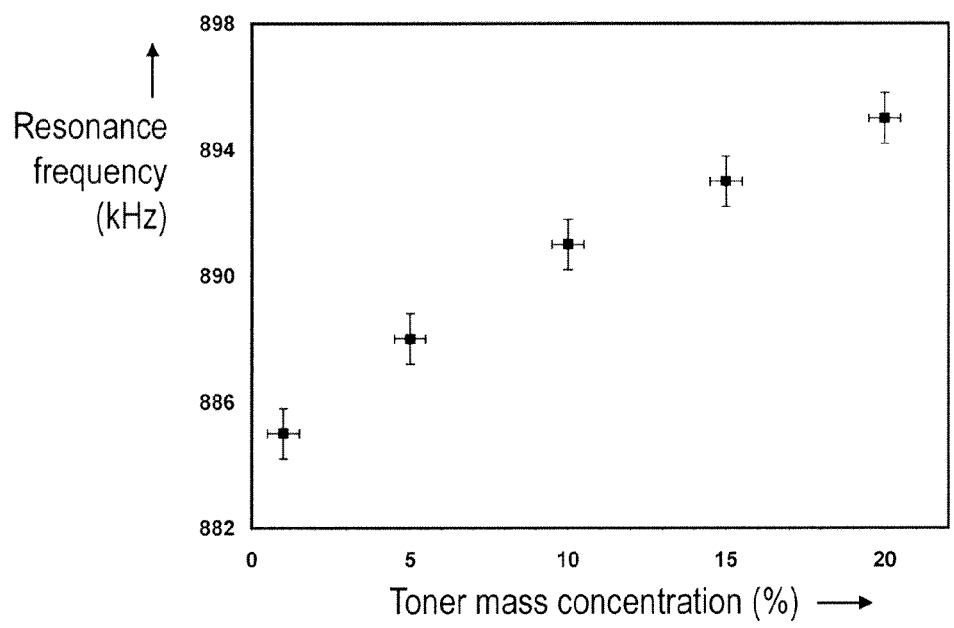
FIG. 4 illustrates a diagram that shows the dependency of the mass concentration of the particles on the resonance frequency of the sound pressure wave in the measurement cell.

Different resonance frequencies result given different mass concentrations TK of the particles in the dispersion. The mass concentration TK of the particles in the dispersion can thus be concluded from the resonance frequency of a dispersion that is determined via measurement. If the dependency of the resonance frequencies on the mass concentrations of the particles in dispersions with known mass concentrations TK is determined in a preceding calibration process, the mass concentration TK can be determined from a measured resonance frequency. FIG. 4 shows an example of such a diagram for liquid developers in which the resonance frequencies have been determined depending on the toner mass concentrations TK given five known toner mass concentrations TK, wherein the temperature and the carrier fluid remain constant. If, given an unknown toner mass concentration of a liquid developer, its resonance frequency is measured with the measurement arrangement according to FIG. 1, the toner concentration TK can be read out via the diagram of FIG. 4. The curve according to FIG. 4 can be stored as a table in the processor unit PR. The toner concentration TK can thus be concluded directly from the resonance frequency, in contrast to a method in which the sound velocity is initially established and then the toner concentration is concluded from the sound velocity via a table determined via a calibration process. The measurement of the sound velocity via the delay of the sound wave in a sample chamber is, however, less precise relative to the determination of the resonance frequency.

In addition to this, according to R. W. O'Brien et. al./Colloids and Surfaces A, the mobility in a sample volume can be determined with the measurement arrangement of FIG. 1 from the evaluation of the ESA signal and the mass concentration TK (obtained via the resonance frequency at a given temperature T). According to the formula (2) it is assumed that the variables ESA (sound pressure amplitude), TK (mass concentration), c (sound velocity of the fluid) and η (viscosity of the fluid) and Δρ (density difference between particles and fluid) are known for the dispersions (liquid developer, for example) to be examined. Given a liquid developer, the liquid is the carrier fluid or the carrier.

The variables influencing the amplitude (ESA) of the sound pressure wave are:

$$ESA = c * \Delta p * TK * \mu_d * G \quad (1)$$

c: is thereby the sound velocity of the liquid in the dispersion
Δp: is the density difference between particles and liquid
TK: is the particle mass concentration
$\mu_d$: is the dynamic mobility of the particles
G: is the calibration factor that includes the properties of the measurement cell MZ, for example.

The value of the dynamic mobility $\mu_d$ of the particles can be calculated from the ESA values as:

$$\mu_d = ESA / c * \Delta p * TK * G \quad (2)$$

G is determined with the calibration of the mobility measurement.

If only the mass concentration TK of the particles should be determined, the excitation of the acoustic wave in the measurement cell MZ can also take place photo-acoustically, for example with an optical radiation (via a laser, for example) at suitable wavelengths in which the dispersion sufficiently absorbs the radiation.

Although a preferred exemplary embodiment is shown and described in detail in the drawings and in the preceding specification, it should be viewed as purely exemplary and not as limiting the invention. It is noted that only a preferred exemplary embodiment is shown and described, and all variations and modifications that presently or in the future lie within the protective scope of the invention should be protected.

I claim as my invention:

1. A method to determine particle mass concentration in a dispersion having particles and fluid, comprising the steps of:
    exposing the dispersion in a measurement cell to an alternating field of variable frequency via which the particles in the dispersion are set into oscillation so that the particles generate sound pressure waves in the dispersion;
    measuring amplitudes of the sound pressure waves depending on the frequencies so that a maximum amplitude of the sound pressure waves is established and a frequency associated with said amplitude is determined as a resonance frequency of the sound pressure wave; and
    establishing the mass concentration of the particles in the dispersion from the resonance frequency.

2. The method according to claim 1 in which the alternating field is generated by an alternating electrical voltage of adjustable frequency.

3. The method according to claim 1 in which the alternating field is generated photoacoustically.

4. The method according to claim 1 in which a dependency of the resonance frequency on the mass concentration is determined in a calibration process, in which dispersions with known mass concentrations are filled into the measurement cell at a given temperature and their resonance frequencies are established and the dependency of the resonance frequencies on the mass concentrations is entered in a table so that the mass concentration of the particles in the dispersion can be read from the table from a measured resonance frequency of the dispersion.

5. The method according to claim 1 in which the dispersion comprises a liquid developer having toner particles and carrier fluid that is used to develop charge images in an electrographic printing apparatus.

6. The method according to claim 1 in which:
the amplitudes of the sound pressure waves are measured in the measurement cell depending on the frequencies, and the measurement values are supplied to a control unit; and
the control unit supplies the measurement values to a processor unit that determines the resonance frequency from the measurement values, determines the mass concentration depending on the resonance frequency, and emits them at an output.

7. The method according to claim 6 in which the control unit determines the electrophoretic mobility of the particles in the dispersion from the mass concentration, the sound pressure amplitude and the known dispersion variables of the sound velocity of the fluid in the dispersion, and a density difference between the particles and the fluid in the dispersion.

8. The method according to claim 7 in which dynamic electrophoretic mobility $\mu_d$ of the particles in the dispersion is determined according to the formula $$\mu_d = ESA/c * \Delta p * TK * G,$$

where
c=sound velocity,
$\Delta p$=the density difference between the particles and the fluid,
TK=the mass concentration, and
G=a calibration factor that is dependent on the frequency.

9. The method according to claim 8 in which the determination of the mass concentration and the electrophoretic mobility $\mu_d$ take place simultaneously in a measurement process.

10. A method to determine particle mass concentration in a liquid developer dispersion having toner particles and carrier fluid to develop charge images in an electrographic printing apparatus, comprising the steps of:
exposing the dispersion in a measurement cell to an alternating field of variable frequency via which the particles in the dispersion are set into oscillation so that the particles generate sound pressure waves in the dispersion, said alternating field being generated by an alternating electrical voltage of adjustable frequency;
measuring amplitudes of the sound pressure waves depending on the frequencies so that a maximum amplitude of the sound pressure waves is established and a frequency associated with said amplitude is determined as a resonance frequency of the sound pressure wave; and
establishing the mass concentration of the particles in the dispersion from the resonance frequency.

\* \* \* \* \*